(12) United States Patent
Rong et al.

(10) Patent No.: US 12,712,467 B2
(45) Date of Patent: Aug. 18, 2026

(54) WIRELESS CHARGING RECTIFIER CIRCUIT, WIRELESS CHARGING DEVICE AND VENTRICULAR ASSIST DEVICE

(71) Applicant: SHENZHEN CORE MEDICAL TECHNOLOGY CO., LTD, Shenzhen (CN)

(72) Inventors: Zhenglai Rong, Shenzhen (CN); Shunzhou Yu, Shenzhen (CN)

(73) Assignee: SHENZHEN CORE MEDICAL TECHNOLOGY CO., LTD, Shenzhen (CN)

( * ) Notice: Subject to any disclaimer, the term of this patent is extended or adjusted under 35 U.S.C. 154(b) by 155 days.

(21) Appl. No.: 18/849,942

(22) PCT Filed: May 6, 2023

(86) PCT No.: PCT/CN2023/092399

§ 371 (c)(1),
(2) Date: Sep. 23, 2024

(87) PCT Pub. No.: WO2024/012022

PCT Pub. Date: Jan. 18, 2024

(65) Prior Publication Data

US 2025/0211127 A1 Jun. 26, 2025

(30) Foreign Application Priority Data

Jul. 12, 2022 (CN) ........................ 202210813918.2

(51) Int. Cl.
*H02M 7/12* (2006.01)
*A61M 60/178* (2021.01)
(Continued)

(52) U.S. Cl.
CPC ............ *H02M 7/12* (2013.01); *A61M 60/178* (2021.01); *A61M 60/247* (2021.01);
(Continued)

(58) Field of Classification Search
CPC ........ H02M 7/12; H02M 1/126; H02M 1/325; H02M 7/05; H02M 7/06; H02M 7/08;
(Continued)

(56) References Cited

U.S. PATENT DOCUMENTS 4,005,350 A * 1/1977 Brenneisen ........... H02M 7/521 363/58
2004/0095785 A1* 5/2004 Balakrishnan .......... H02M 1/44 363/44

(Continued)

FOREIGN PATENT DOCUMENTS

CN 1794566 A 6/2006
CN 101572488 A 11/2009

(Continued)

OTHER PUBLICATIONS

Notice of Reasons for Refusal issued for Japanese Patent Application No. 2024-560816, Dispatch date: Dec. 2, 2025, 12 pages including English machine translation.

(Continued)

*Primary Examiner* — Yusef A Ahmed
(74) *Attorney, Agent, or Firm* — HSML.P.C.

(57) ABSTRACT

A wireless charging rectifier circuit, a wireless charging device and a ventricular assist device are disclosed. The wireless charging rectifier circuit includes a first filter circuit, a bridge rectifier circuit and a second filter circuit which are connected in sequence, each bridge arm of four bridge arms of the bridge rectifier circuit being connected to a first diode and at least one second diode which are connected in parallel, and the at least one second diode being used to perform rectification when the first diode connected in parallel fails.

13 Claims, 3 Drawing Sheets

(51) Int. Cl.

| | |
|---|---|
| ***A61M 60/247*** | (2021.01) |
| ***A61M 60/424*** | (2021.01) |
| ***A61M 60/873*** | (2021.01) |
| ***H02J 50/10*** | (2016.01) |
| ***H02J 50/12*** | (2016.01) |
| ***H02M 1/12*** | (2006.01) |
| ***H02M 1/32*** | (2007.01) |
| ***H02M 7/04*** | (2006.01) |
| ***H02M 7/06*** | (2006.01) |
| *H02M 7/08* | (2006.01) |

(52) U.S. Cl.
CPC ........ *A61M 60/424* (2021.01); *A61M 60/873* (2021.01); *H02J 50/10* (2016.02); *H02J 50/12* (2016.02); *H02M 1/126* (2013.01); *H02M 1/325* (2021.05); *H02M 7/05* (2021.05); *H02M 7/06* (2013.01); *H02M 7/08* (2013.01)

(58) Field of Classification Search
CPC ...... H02M 1/14; H02M 1/143; A61M 60/178; A61M 60/247; A61M 60/424; A61M 60/873; H02J 50/10; H02J 50/12; H02J 7/60; H02J 2207/20; Y02B 70/10
See application file for complete search history.

(56) References Cited

U.S. PATENT DOCUMENTS

| | | | | |
|---|---|---|---|---|
| 2011/0044035 | A1* | 2/2011 | Chen | H02M 7/08 363/126 |
| 2012/0155134 | A1* | 6/2012 | Kim | H02J 50/70 363/84 |
| 2012/0170337 | A1* | 7/2012 | Lisi | H02J 50/12 363/126 |
| 2012/0293009 | A1* | 11/2012 | Kim | H02H 7/1252 307/104 |
| 2012/0294054 | A1* | 11/2012 | Kim | H02J 50/80 363/126 |
| 2013/0077360 | A1* | 3/2013 | Low | H02J 50/90 363/47 |
| 2013/0077361 | A1* | 3/2013 | Low | H02J 50/12 363/47 |
| 2013/0128638 | A1* | 5/2013 | Irish | H02J 50/12 363/126 |
| 2014/0126260 | A1* | 5/2014 | Amrutur | H02M 7/217 363/127 |
| 2014/0177305 | A1* | 6/2014 | Irish | H02M 7/219 363/127 |
| 2015/0263539 | A1* | 9/2015 | Irish | H02M 1/4208 307/104 |
| 2016/0204619 | A1* | 7/2016 | Lin | H01F 38/14 307/104 |
| 2017/0047781 | A1* | 2/2017 | Stanislawski | H02J 50/12 |
| 2017/0187244 | A1* | 6/2017 | Su | H02J 50/12 |
| 2017/0280525 | A1* | 9/2017 | Barbosa | H02J 9/061 |
| 2018/0159380 | A1* | 6/2018 | Il | H02J 50/12 |
| 2018/0351349 | A1* | 12/2018 | Rajagopalan | H02H 7/125 |
| 2019/0021154 | A1* | 1/2019 | Sadwick | H05B 45/34 |
| 2019/0149060 | A1* | 5/2019 | Tritschler | H02M 7/219 307/31 |
| 2019/0157907 | A1* | 5/2019 | Sugiyama | H02J 50/80 |
| 2019/0165611 | A1* | 5/2019 | Miyazawa | H02J 50/12 |
| 2019/0305613 | A1* | 10/2019 | Oshima | H02J 50/12 |
| 2021/0313901 | A1* | 10/2021 | Huang | H03K 17/687 |
| 2022/0166246 | A1* | 5/2022 | Han | H02M 3/07 |
| 2022/0278555 | A1* | 9/2022 | Liu | H02M 7/217 |
| 2023/0023680 | A1* | 1/2023 | Wu | H02J 50/12 |
| 2023/0040473 | A1* | 2/2023 | Gu | H02J 7/64 |
| 2023/0065766 | A1* | 3/2023 | Pei | H02J 50/12 |
| 2023/0103414 | A1* | 4/2023 | Xiao | H02J 7/933 320/108 |

FOREIGN PATENT DOCUMENTS

| | | | |
|---|---|---|---|
| CN | 204481681 | U | 7/2015 |
| CN | 105529938 | A | 4/2016 |
| CN | 205490192 | U | 8/2016 |
| CN | 205725460 | U | 11/2016 |
| CN | 205811851 | U | 12/2016 |
| CN | 206209828 | U | 5/2017 |
| CN | 107776429 | A | 3/2018 |
| CN | 108173299 | A | 6/2018 |
| CN | 108463022 | A | 8/2018 |
| CN | 208112510 | U | 11/2018 |
| CN | 109450268 | A | 3/2019 |
| CN | 208608910 | U | 3/2019 |
| CN | 209200949 | U | 8/2019 |
| CN | 210669913 | U | 6/2020 |
| CN | 210745047 | U | 6/2020 |
| CN | 112003483 | A | 11/2020 |
| CN | 112187070 | A | 1/2021 |
| CN | 212627329 | U | 2/2021 |
| CN | 212627699 | U | 2/2021 |
| CN | 113497613 | A | 10/2021 |
| CN | 113991887 | A | 1/2022 |
| CN | 114900055 | A | 8/2022 |
| JP | S5597101 | A | 7/1980 |
| JP | S57163145 | U | 10/1982 |
| JP | S649495 | U | 1/1989 |
| JP | H08162368 | A | 6/1996 |
| JP | H09153428 | A | 6/1997 |
| JP | H10132835 | A | 5/1998 |
| JP | 2000012382 | A | 1/2000 |
| JP | 2000308261 | A | 11/2000 |
| JP | 2002118963 | A | 4/2002 |
| JP | 2012033544 | A | 2/2012 |
| JP | 2013042072 | A | 2/2013 |
| JP | 2016077088 | A | 5/2016 |
| JP | 2019017216 | A | 1/2019 |
| WO | 2019097699 | A1 | 5/2019 |
| WO | 2021082586 | A1 | 5/2021 |
| WO | 2022140242 | A1 | 6/2022 |

OTHER PUBLICATIONS

International Search Report issued for International Patent Application No. PCT/CN2023/092399, Date of mailing: Jun. 21, 2023, 7 pages including English translation.

Written Opinion issued for International Patent Application No. PCT/CN2023/092399, Date of mailing: Jun. 21, 2023, 6 pages including English machine translation.

Office Action issued for Chinese Patent Application No. 202210813918.2, dated Aug. 23, 2022, 8 pages.

Supplemental Search Report issued for Chinese Patent Application No. 202210813918.2, dated Aug. 30, 2022, 2 pages.

Hachisuka, M. et al., "Inverter-rectifier using SiC power devices for bidirectional wireless power transfer system of electric vehicles," Materials Science Forum, vols. 778-780, 2014, pp. 1100-1103.

Extended European Search Report issued for European Patent Application No. 23838519.9, dated May 28, 2025, 10 pages.

* cited by examiner

WIRELESS CHARGING RECTIFIER CIRCUIT, WIRELESS CHARGING DEVICE AND VENTRICULAR ASSIST DEVICE

CROSS-REFERENCE TO RELATED APPLICATION

The present application a US national stage application of PCT international application PCT/CN2023/092399, filed on May 6, 2023, which claims priority to Chinese Patent Application with No. 202210813918.2, entitled "Wireless Charging Rectifier Circuit, Wireless Charging Device and Ventricular Assist Device", and filed on Jul. 12, 2022, the content of which is expressly incorporated herein by reference in its entirety.

TECHNICAL FIELD

The present disclosure relates to the field of wireless charging technology, particularly to a wireless charging rectifier circuit, a wireless charging device and a ventricular assist device.

BACKGROUND

A ventricular assist device is an artificial mechanical device that draws blood from the venous system or the heart and pumps the blood directly into the arterial system to partially or completely replace the ventricular work, so that sufficient blood supply power can be provided for patients with serious heart problems.

In order to reduce the risk of infection caused by subcutaneous drilling of wire holes, the existing ventricular assist devices use wireless charging devices to power the blood pump and/or the driving circuit that drives the blood pump in the body. The wireless charging device includes a transmitting unit and a receiving unit. The receiving unit is arranged in the human body and the transmitting unit is arranged outside the human body. The transmitting unit charges the receiving unit through magnetic coupling resonance between the a transmitting coil and a receiving coil.

SUMMARY

The purpose of the present disclosure is to provide a wireless charging rectifier circuit, a wireless charging device, and a ventricular assist device.

In the first aspect of the present disclosure, a wireless charging rectifier circuit is provided, which is configured to rectify and filter an alternating current signal of the ventricular assist device, and includes a first filter circuit, a bridge rectifier circuit, and a second filter circuit connected in sequence; each of four bridge arms of the bridge rectifier circuit is respectively connected to a first diode and at least one second diode which are connected to each other in parallel, and the at least one second diode is configured to perform rectification when the parallel first diode fails.

In the second aspect of the present disclosure, a wireless charging device is provided, which includes the wireless charging rectifier circuit as described in the above first aspect.

In the third aspect of the present disclosure, a ventricular assist device is provided, which includes the wireless charging rectifier circuit as described in the above first aspect or the wireless charging device as described in the above second aspect.

The details of one or more embodiments of the present disclosure are set forth in the accompanying drawings and the description below. Other features, purposes, and advantages of the present disclosure will be obvious from the specification, drawings, and claims.

BRIEF DESCRIPTION OF THE DRAWINGS

In order to more clearly illustrate the technical solution in the embodiments of the present disclosure, the accompanying drawings required for use in the embodiments or in the existing technologies will be briefly introduced below. Obviously, the drawings described below are merely some embodiments of the present disclosure. Those skilled in the art may obtain other drawings based on these drawings without any creative effort.

DETAILED DESCRIPTION

In order to make the technical problem, the technical solution and advantages of the present disclosure clearer to understand, the present disclosure is elaborated below in conjunction with the accompanying drawings and embodiments. It should be appreciated that the specific embodiments described herein are merely used for explaining the present disclosure, rather than limiting the present disclosure.

In addition, the terms "first" and "second" are used for descriptive purposes only and should not be understood as indicating or implying relative importance or implicitly indicating the quantity of the indicated technical features. Therefore, features defined as "first" or "second" may explicitly or implicitly include one or more of such features. In the description of the present disclosure, "plurality" means two or more than two, unless otherwise clearly and specifically defined.

Figure 1:
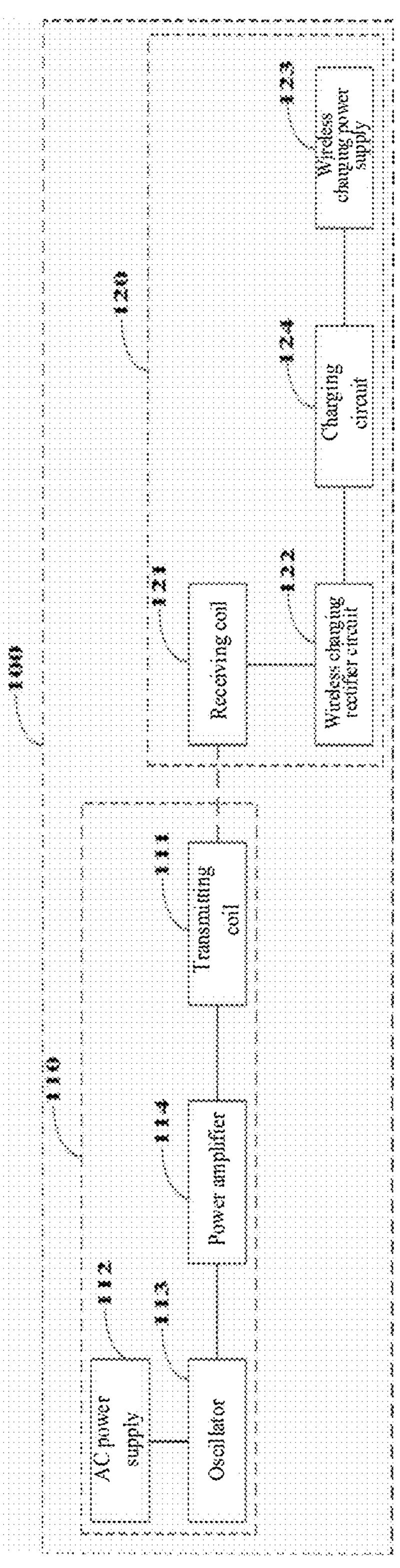
FIG. 1 is a schematic module diagram of a wireless charging circuit according to an embodiment of the present disclosure.

Referring to FIG. 1, which shows a wireless charging circuit 100 provided in an embodiment of the present disclosure. The wireless charging circuit 100 is applied to a ventricular assist device and is configured to charge the ventricular assist device. As shown in FIG. 1, the wireless charging circuit 100 may include a transmitting unit 110 and a receiving unit 120. The receiving unit 120 is provided in the body of a user and is electrically connected to a battery of the implantable ventricular assist device in the body of the user. The transmitting unit 110 is provided outside the body of the user.

The transmitting unit 110 includes a transmitting coil 111, and the receiving unit 120 includes a receiving coil 121. The center of the transmitting coil 111 is located on the same horizontal line as the center of the receiving coil 121, and the resonant frequency of the transmitting coil 111 is the same as that of the receiving coil 121. The transmitting unit 110 can charge the receiving unit 120 through magnetic coupling resonance between the transmitting coil 111 and the receiving coil 121, thereby charging the ventricular assist device. That is to say, the transmitting coil 111 is configured to generate an alternating magnetic field and couple the alternating magnetic field to the receiving coil 121. The receiving coil 121 induces a high-frequency voltage signal through the alternating magnetic field generated by the transmitting coil 111. The high-frequency voltage signal induced by the receiving coil 121 is denoted as AC, accordingly the implantable ventricular assist device in the body of the user is charged.

For example, the transmitting unit 110 may further include an alternating current (AC) power supply 112, an oscillator 113, and a power amplifier 114. An output terminal of the AC power supply 112 is electrically connected to an input terminal of the oscillator 113, an output terminal of the oscillator 113 is electrically connected to an input terminal of the power amplifier 114, and the output terminal of the power amplifier 114 is electrically connected to an input terminal of the transmitting coil 111. In the embodiment, the AC power supply 112 is configured to input 220V power frequency alternating current, the oscillator 113 is configured to generate a high-frequency sine wave for transmitting wireless power, and the power amplifier 114 is configured to amplify a power of the high-frequency sine wave transmitted by the oscillator, in order to satisfy the requirement for wireless power transmission of the human implantable ventricular assist device, that is, to implement a stable supply of a voltage signal to the transmitting coil 111, and then the transmitting coil 111 may generate the alternating magnetic field according to the alternating signal of the amplified power transmitted by the power amplifier 114.

For example, the receiving unit 120 may further include a wireless charging rectifier circuit 122 and a wireless charging power supply 123. The wireless charging rectifier circuit 122 is provided in the human body and is configured to rectify and filter the AC signal transmitted by the ventricular assist device.

Furthermore, the receiving unit 120 may further include a charging circuit 124. An output terminal of the receiving coil 121 is electrically connected to an input terminal of the wireless charging rectifier circuit 122, an output terminal of the wireless charging rectifier circuit 122 is electrically connected to an input terminal of the charging circuit 124, and an output terminal of the charging circuit 124 is electrically connected to an input terminal of the wireless charging power supply 123 to charge the wireless charging power supply 123. The wireless charging power supply 123 is a battery of the implantable ventricular assist device. In the embodiment, the wireless charging rectifier circuit 122 is configured to convert the AC signal transmitted by the receiving coil 121 into a direct current (DC) signal, and perform smoothing to stabilize the DC signal until the outputted signal is a stable DC signal. The charging circuit 124 is configured to provide a dynamically changing current for the wireless charging power supply 123.

For example, the ventricular assist device may further include a monitoring device provided outside the human body. The monitoring device includes electrodes, a signal processing circuit and a communication circuit connected in sequence. The electrodes are attached to the human skin to sense the heartbeat of the human body and generate a corresponding electrical signal. The signal processing circuit is configured to perform signal processing and determination on the electrical signal, and feed a determination result back to a terminal device through the communication circuit.

At present, the wireless rectifier circuit during the wireless charging has low safety. When one of the diodes fails, the wireless rectifier circuit may have a short circuit or overload problem, resulting in failure of rectification, reduced reliability and safety, and inability to power the ventricular assist device and/or the drive circuit, which causes abnormal operation of the ventricular assist device, thereby affecting the life safety of the patient.

Figure 2:
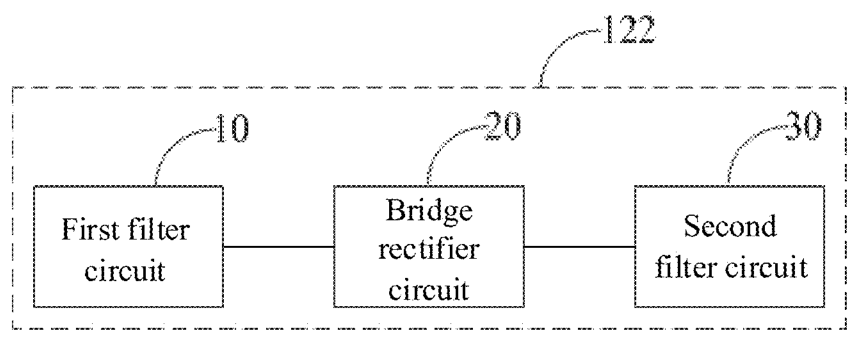
FIG. 2 is a schematic module diagram of a wireless charging rectifier circuit according to an embodiment of the present disclosure.

In view of this, with reference to FIG. 2, which is a schematic structure diagram of the wireless charging rectifier circuit 122 provided in an embodiment of the present disclosure. The wireless charging rectifier circuit 122 is provided in the human body and is configured to rectify and filter the AC signal of the ventricular assist device. The wireless charging rectifier circuit 122 may include a first filter circuit 10, a bridge rectifier circuit 20 and a second filter circuit 30 connected in sequence. The first filter circuit 10 is configured to perform input filtering on the inputted AC signal. The second filter circuit 30 is configured to perform output filtering on a DC power supply outputted by the bridge rectifier circuit 20. The bridge rectifier circuit 20 is configured to rectify the input AC signal and output the corresponding DC power supply, thereby reducing interference of an interference signal on a subsequent circuit of the wireless charging rectifier circuit 122 and improving the reliability and safety of the ventricular assist device.

Figure 3:
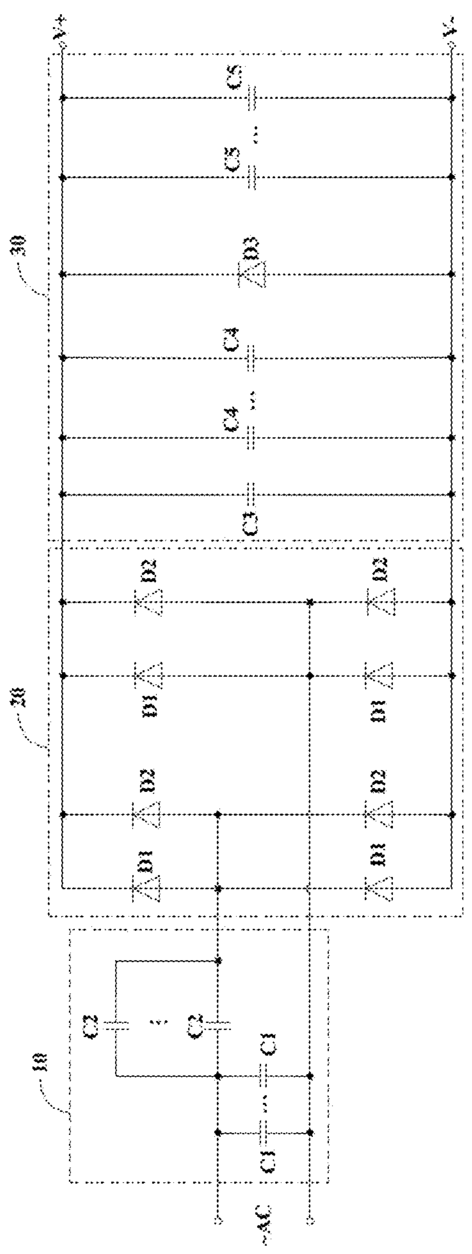
FIG. 3 is a schematic diagram of a wireless charging rectifier circuit according to an embodiment of the present disclosure.

As shown in FIG. 3, the bridge rectifier circuit 20 includes four symmetrical bridge arms. Diagonal bridge arms constitute a half-wave rectifier to rectify one half-wave AC power supply of the wireless AC power supply. Two diagonal bridge arms constitute a full-bridge rectifier. Each of the four bridge arms is respectively connected to a first diode D1 and at least one second diode D2 which are connected to each other in parallel. The at least one second diode D2 is configured to rectify when the first diode D1 in parallel fails. The first diode D1 serves as a main diode, and the first diodes D1 of the four bridge arms rectify the AC signal during the normal operation. The at least one second diode D2 serves as a backup diode. When one of the first diodes D1 fails, such as open circuit or burnout, the second diode D2 connected to the failed first diode D1 is put into rectification operation, and forms a new wireless charging rectifier circuit 122 with the remaining first diodes D1 and/or second diodes D2 to rectify the AC signal, thereby implementing redundant rectification conversion and improving the reliability and safety of the rectification of the wireless charging rectifier circuit 122 and the ventricular assist device.

The first diode D1 and the second diode D2 can be different types of diodes to achieve the redundancy, or a corresponding detection circuit is connected in parallel between the parallel first diode D1 and the second diode D2. When a failure of the first diode D1 is detected, the second diode D2 is controlled to form a corresponding bridge arm in the wireless charging rectifier circuit 122 to implement the rectification operation of the wireless charging rectifier circuit 122. The specific types and structures of the first diode D1 and the second diode D2 are not limited.

In an embodiment, a diode with a first turn-on voltage drop and a second diode D2 with a second turn-on voltage drop are selected, and the turn-on voltage drop of the first diode D1 is smaller than the turn-on voltage drop of the second diode D2. During the normal operation of the wireless charging rectifier circuit 122, that is, when each of the first diodes D1 is not faulty, since the turn-on voltage drop of the first diode D1 is greater than the turn-on voltage drop of at least one second diode D2, the first diode D1 on each bridge arm in the wireless charging rectifier circuit 122 is turned on first, accordingly a rectifier circuit is formed, and the inputted AC signal is rectified by the first diodes D1 with the first turn-on voltage drop. The second diode D2 does not operate when connected in parallel with the first diode D1 due to the larger turn-on voltage drop thereof.

Furthermore, when the first diode D1 fails, at least one second diode D2 connected in parallel with the failed first diode D1 performs filtering and rectification. In other words, when the first target diode D1 fails, the second target diode D2 and the remaining first diodes D1 and/or second diodes D2 are turned on to form a rectifier circuit to perform the rectification, thereby rectifying the AC signal and implementing the redundant rectification conversion, improving the rectification reliability and safety of the wireless charging rectifier circuit 122 and the ventricular assist device.

The first target diode D1 is the first diode D1 on any bridge arm, and the second target diode D2 is any one of at least one second diode D2 connected in parallel with the first target diode D1, that is, the first target diode D1 can be one or more of the four first diodes D1, and the second target diode D2 is the second diode D2 connected to the faulty first diode D1 for redundancy, and serves as a backup rectifier diode to perform the rectification.

Different types of diodes may be selected according to requirements for the turn-on voltage drops of the first diode D1 and the second diode D2. Optionally, the first diode D1 is an ideal diode, and the second diode D2 is a Schottky diode.

In the embodiment of the present disclosure, the turn-on voltage drop of the ideal diode is smaller, and the turn-on voltage drop of the Schottky diode is larger. Since the ideal diode is connected to the Schottky diode in parallel to form active-backup diodes, a dual rectification design is achieved, accordingly the reliability and safety of the wireless charging rectifier circuit is improved. Meanwhile, at least one Schottky diode is adopted for the redundant design, which not only further improves the reliability and safety of the wireless charging rectifier circuit, but also increases the service life of the wireless charging rectifier circuit, thereby extending the service life of the ventricular assist device.

Furthermore, when the wireless charging rectifier circuit 122 operates normally, the rectification operation is performed by the ideal diodes with a smaller turn-on voltage drop, which can reduce the power consumption and heat generation of the wireless charging rectifier circuit 122, accordingly a larger amount of heat may not be generated in the body, the heat dissipation problem of the wireless charging rectifier circuit 122 is solved, thereby improving the safety of the wireless charging rectifier circuit 122, ensuring the normal operation of the ventricular assist device, and ensuring the safety of the patient.

When one or more of the ideal diodes fails, the corresponding parallel Schottky diodes perform the rectification to ensure the rectifier circuit to continue the rectification operation and provide an operational power supply to a corresponding module in the ventricular assist device located in the human body.

The number of Schottky diodes can be provided according to requirements, such as one or more Schottky diodes, and the specific number is not limited herein.

As for the first filter circuit 10 and the second filter circuit 30, the corresponding filter capacitors, filter inductors and other structures can be selected according to frequency bands of the inputted and outputted power signals, and the specific structures are not limited herein.

Optionally, as shown in FIG. 3, the first filter circuit 10 may include a plurality of first capacitors C1 in parallel and a plurality of second capacitors C2 in parallel. One terminal of the plurality of first capacitors C1 in parallel is connected to the first input terminal of the first filter circuit 10 and one terminal of the plurality of second capacitors C2 in parallel respectively, the other terminal of the plurality of first capacitors C1 in parallel is connected to the second input terminal of the first filter circuit 10 and the second output terminal of the first filter circuit 10 respectively, and the other terminal of the plurality of second capacitors C2 in parallel is connected to the first output terminal of the first filter circuit 10.

In the embodiment, the first capacitor C1 is connected in parallel between the input terminals of the first filter circuit 10. The input terminals of the first filter circuit 10 are connected to the receiving coil 121. The first capacitor C1 serves as a filter capacitor and is configured to filter the AC signal outputted by the receiving coil 121 and eliminate a peak overshoot signal. The first capacitors C1 provide a redundant filter capacitor configuration. When one of the first capacitors C1 is damaged, the remaining first capacitors C1 can also perform the filtering operation, thereby improving the reliability and safety of the wireless charging rectifier circuit 100.

Specifically, the plurality of second capacitors C2 and the receiving coil 121 form an LC resonant circuit, which is configured to sense the high-frequency alternating magnetic field generated by the transmitting coil 111 and resonate to generate a high-frequency voltage signal. The wireless charging rectifier circuit 122 is configured to rectify the high-frequency voltage signal into a DC signal, and the DC signal is filtered through the second filter circuit 30 before being outputted to the subsequent module.

In order to filter the high-frequency voltage signal, optionally, a capacitance of the first capacitor C1 is smaller than a capacitance of the second capacitor C2. The first capacitor C1 filters a higher-frequency interference signal and avoids filtering the high-frequency voltage signal, thereby achieving the filtering compensation and improving the filtering capability.

At the same time, the capacitances of the plurality of first capacitors C1 may be the same or different. When the capacitances of the plurality of first capacitors C1 are different, high-frequency interference signals in different frequency bands can be filtered, thereby improving the filtering range.

Optionally, as shown in FIG. 3, the second filter circuit 30 may include a third capacitor C3, a plurality of fourth capacitors C4 in parallel, a third diode D3, and a plurality of fifth capacitors C5 in parallel.

One terminal of the third capacitor C3 is connected to the first input terminal of the second filter circuit 30, one terminal of the plurality of fourth capacitors C4 in parallel, an anode of the third diode D3, one terminal of the plurality of fifth capacitors C5 in parallel, and the first output terminal of the second filter circuit 30 respectively. The other terminal of the third capacitor C3 is connected to the second input terminal of the second filter circuit 30, the other terminal of the plurality of fourth capacitors C4 in parallel, a cathode of the third diode D3, the other terminal of the plurality of fifth capacitors C5 in parallel, and the second output terminal of the second filter circuit 30.

In the embodiment, the third capacitor C3, the fourth capacitor C4 and the fifth capacitor C5 complete the filtering operation. The fourth capacitor C4 and the fifth capacitor C5 constitute redundant filter capacitors. When the third capacitor C3 and/or the third diode D3 is damaged, the fourth capacitor C4 and the fifth capacitor C5 continue to perform the filtering operation, accordingly the normal filtering operation of the second filter circuit 30 is guaranteed.

At the same time, in order to filter signals in different frequency bands, optionally, the capacitance of the fourth capacitor C4 is smaller than the capacitance of the third capacitor C3 and smaller than the capacitance of the fifth capacitor C5. The fourth capacitor C4 can filter the higher-frequency interference signal, accordingly the filtering compensation can be implemented, and the filtering capability is improved.

The third diode D3 may be a Zener diode to implement the output voltage stabilization function.

Furthermore, in order to simplify the overall structure of the wireless charging rectifier circuit 122 and the ventricular assist device, optionally, the first diode D1, the second diode D2, the third diode D3, the first capacitors C1, the second capacitors C2, the third capacitor C3, the fourth capacitors C4, and the fifth capacitors C5 are all surface mount devices (SMDs). The SMD can effectively reduce the volumes of the wireless charging rectifier circuit 122 and the ventricular assist device, reduce the area of the wireless charging rectifier circuit 122, and reduce the design cost, which is more reliable in the redundant design.

Compared to the prior art, the embodiments of the present disclosure have the following advantages: each bridge arm of the wireless charging rectifier circuit 122 includes a first diode D1 and at least one second diode D2 in parallel, the first diode D1 serves as a main diode. During the normal operation, the first diode D1 is configured to rectify the AC signal, the second diode D2 serves as a backup diode and rectifies the AC signal when the first diode D1 fails, thereby implementing the redundant rectification conversion, and improving the rectification reliabilities and safeties of the wireless charging rectifier circuit 122 and the ventricular assist device. Meanwhile, the first filter circuit 10 and the second filter circuit 30 filter the input power supply and the output power supply of the wireless charging rectifier circuit 122, thereby reducing the interference of the interference signals on the subsequent circuit of the wireless charging rectifier circuit 122, and further improving the reliability and safety of the ventricular assist device.

The present disclosure further provides a wireless charging device, which includes the wireless charging rectifier circuit 122. As for the specific structure of the wireless charging rectifier circuit 122, reference can be made to the above embodiments. Since the wireless charging device adopts all the technical solution of all the above embodiments, the wireless charging device has at least all the advantages brought by the technical solution of the above embodiments, which will not be repeated here.

The embodiments described above are only used for illustrating the technical solution of the present disclosure, rather than limiting it. Although the present disclosure is elaborated with reference to the aforementioned embodiments, a person skilled in the art should understand that the technical solution described in the aforementioned embodiments may still be modified, or some of the technical features may be replaced by equivalents. Such modifications or replacements do not cause the corresponding technical solution to essentially deviate from the spirit and scope of the technical solution of the embodiments of the present disclosure, and should all fall within the protection scope of the present disclosure.

What is claimed is:

1. A wireless charging rectifier circuit, comprising a first filter circuit, a bridge rectifier circuit, and a second filter circuit connected in sequence, wherein each of four bridge arms of the bridge rectifier circuit is respectively connected to a first diode and at least one second diode which are connected to each other in parallel, and the at least one second diode is configured to perform rectification when the parallel first diode fails, wherein a turn-on voltage drop of each of the first diodes is smaller than a turn-on voltage drop of each of the at least one second diodes; and when the wireless charging rectifier circuit operates normally, the first diode on each of the four bridge arms in the bridge rectifier circuit is turned on to form a rectifier circuit to perform the rectification; and when a first target diode fails, a second target diode is turned on to form the rectifier circuit to perform the rectification, the first target diode is the first diode on one of the four bridge arms, and the second target diode is one of the at least one second diode connected in parallel with the first target diode, wherein the first filter circuit comprises a plurality of first capacitors in parallel and a plurality of second capacitors in parallel; and one terminal of the plurality of first capacitors in parallel is connected to a first input terminal of the first filter circuit and one terminal of the plurality of second capacitors in parallel respectively, the other terminal of the plurality of first capacitors in parallel is connected to a second input terminal of the first filter circuit and a second output terminal of the first filter circuit respectively, and the other terminal of the plurality of second capacitors in parallel is connected to a first output terminal of the first filter circuit, and wherein the second filter circuit comprises a third capacitor, a plurality of fourth capacitors in parallel, a third diode, and a plurality of fifth capacitors in parallel; and one terminal of the third capacitor is connected to a first input terminal of the second filter circuit, one terminal of each of the plurality of fourth capacitors in parallel, an anode of the third diode, one terminal of each of the plurality of fifth capacitors in parallel, and a first output terminal of the second filter circuit respectively; the other terminal of the third capacitor is connected to a second input terminal of the second filter circuit, the other terminal of each of the plurality of fourth capacitors in parallel, a cathode of the third diode, the other terminal of each of the plurality of fifth capacitors in parallel, and a second output terminal of the second filter circuit.

2. The wireless charging rectifier circuit according to claim 1, wherein one of the plurality of first capacitors is a filter capacitor.

3. The wireless charging rectifier circuit according to claim 1, wherein a capacitance of one of the plurality of first capacitors is smaller than a capacitance of one of the plurality of second capacitors.

4. The wireless charging rectifier circuit according to claim 1, wherein capacitances of the plurality of first capacitors are different.

5. The wireless charging rectifier circuit according to claim 1, wherein when one of the plurality of first capacitors is damaged, the remaining first capacitors of the plurality of first capacitors are configured to perform filtering of the first filter circuit.

6. The wireless charging rectifier circuit according to claim 1, wherein a capacitance of one of the plurality of fourth capacitors is smaller than a capacitance of the third capacitor and smaller than a capacitance of one of the plurality of fifth capacitors.

7. The wireless charging rectifier circuit according to claim 1, wherein when at least one of the third capacitor and the third diode fails, one of the plurality of fourth capacitors and one of the plurality of fifth capacitors are configured to perform filtering of the second filter circuit.

8. The wireless charging rectifier circuit according to claim 1, wherein the third diode is a Zener diode.

9. The wireless charging rectifier circuit according to claim 1, wherein each of the first diodes, each of the at least one second diodes, the third diode, each of the plurality of first capacitors, each of the plurality of second capacitors, the third capacitor, each of the plurality of fourth capacitors and each of the plurality of fifth capacitors are surface mount devices.

10. The wireless charging rectifier circuit according to claim 1, wherein each of the first diodes is an ideal diode.

11. The wireless charging rectifier circuit according to claim 1, wherein each of the at least one second diodes is a Schottky diode.

12. A wireless charging device, comprising the wireless charging rectifier circuit of claim 1.

13. A ventricular assist device, comprising the wireless charging device of claim 12.

* * * * *